United States Patent
Danzer et al.

(10) Patent No.: US 9,966,409 B2
(45) Date of Patent: May 8, 2018

(54) IMAGING DEVICE FOR ELECTROMAGNETIC RADIATION

(71) Applicant: Siemens Aktiengesellschaft, München (DE)

(72) Inventors: Ludwig Danzer, Wendelstein (DE); Miguel Labayen De Inza, Forchheim (DE); Jan Wrege, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 67 days.

(21) Appl. No.: 14/792,715

(22) Filed: Jul. 7, 2015

(65) Prior Publication Data

US 2016/0015339 A1  Jan. 21, 2016

(30) Foreign Application Priority Data

Jul. 15, 2014 (DE) .................... 10 2014 213 734

(51) Int. Cl.
  *H01L 27/146* (2006.01)
  *A61B 6/00* (2006.01)

(52) U.S. Cl.
  CPC ...... *H01L 27/14661* (2013.01); *A61B 6/4241* (2013.01)

(58) Field of Classification Search
  CPC .............................................. H01L 27/14661
  See application file for complete search history.

(56) References Cited

U.S. PATENT DOCUMENTS

| | | | |
|---|---|---|---|
| 6,933,505 B2 | 8/2005 | Vuorela | |
| 2003/0155516 A1 | 8/2003 | Spartiotis et al. | |
| 2004/0195640 A1 | 10/2004 | Nascetti et al. | |
| 2008/0203313 A1* | 8/2008 | Harrison | G01T 1/247 250/371 |
| 2011/0309259 A1* | 12/2011 | Kim | G01T 1/24 250/370.09 |
| 2012/0146016 A1* | 6/2012 | Park | H01L 23/481 257/42 |
| 2016/0154124 A1* | 6/2016 | Luhta | H01L 27/14618 250/361 R |

FOREIGN PATENT DOCUMENTS

| | | |
|---|---|---|
| CN | 1636278 A | 7/2005 |
| CN | 102544032 A | 7/2012 |
| DE | 102008050838 A1 | 10/2009 |
| DE | 102012202500 A1 | 8/2013 |

OTHER PUBLICATIONS

German Office Action dated Aug. 13, 2015.
"CdZnTe detector array for a scanning-beam digital x-ray system", in: Preprint of manuscript presented at the SPIE Physics of Medical Imaging Conference, 1999.

* cited by examiner

*Primary Examiner* — Christine Sung
(74) *Attorney, Agent, or Firm* — Harness, Dickey & Pierce, P.L.C.

(57) ABSTRACT

An imaging device for electromagnetic radiation, especially for x-ray and/or gamma radiation, is disclosed. In an embodiment, the imaging device includes a layering including a number of detection elements, a number of read-out boards and a base board. Each of the detection elements is electrically contacted with a respective read-out board via a plurality of first solder contacts. Each read-out board includes a plurality of through-contacts and is electrically contacted with the base board via a plurality of second solder contacts.

21 Claims, 1 Drawing Sheet

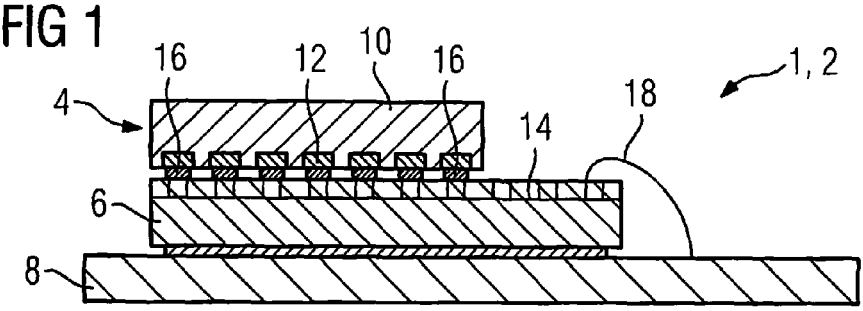
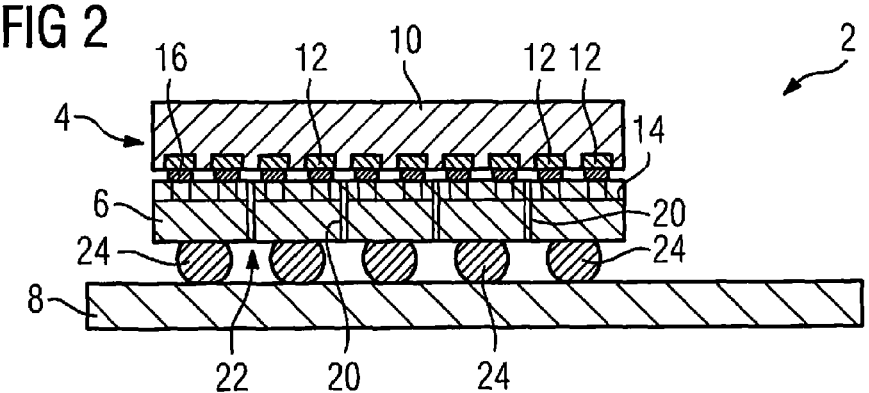
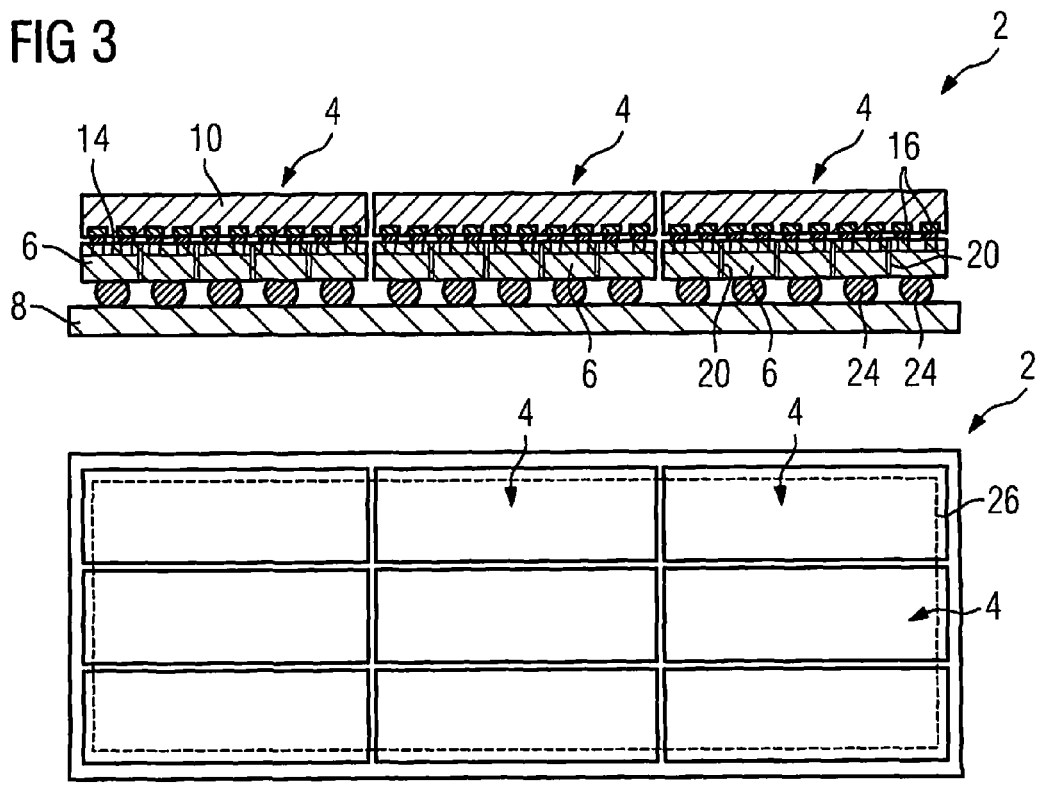

IMAGING DEVICE FOR ELECTROMAGNETIC RADIATION

PRIORITY STATEMENT

The present application hereby claims priority under 35 U.S.C. § 119 to German patent application number DE 102014213734.9 filed Jul. 15, 2014, the entire contents of which are hereby incorporated herein by reference.

FIELD

At least one embodiment of the invention generally relates to an imaging device for electromagnetic radiation, especially for x-ray and/or gamma radiation, wherein the device includes a number of detection elements, a number of read-out boards and a base board.

BACKGROUND

In the field of medical x-ray diagnostics the development of high-resolution radiation detectors is of decisive importance for the meaningfulness of recordings of a medical imaging device and thus ultimately also for the possibilities of diagnosis.

While the advantages of a high spatial resolution capability are obvious here, for many medical applications a good resolution of different radiation energies is also required, for example in order to be able to detect different tissue structures, of which the absorption capability can depend on the energy spectrum of the incident radiation. In order to subject the patient to the lowest possible radiation dose with the highest possible resolution, a high radiation sensitivity in the relevant spectral range is also increasingly important.

Indirect detectors in which the incident radiation is first converted into lower-energy radiation by a scintillator material and the radiation is subsequently detected by photodiodes frequently have a lower effective spatial resolution in this context.

Against this background, direct-converting detectors represent a possible alternative. In a direct-converting detector an incident radiation creates a plurality of band transitions in a fine semiconductor layer, wherein the electrons becoming free can be tapped off at individual electrodes which are attached to the side of the semiconductor facing away from the radiation.

Each electrode here corresponds to a pixel and can in such cases be in contact with read-out electronics, e.g. an ASIC, which is attached to a circuit board in parallel to the semiconductor layer. The contacting can for example be soldered here or achieved by conductive adhesive materials. To improve stability the read-out board for its part can be mounted on a base board, via which the individual signals from the read-out board are also forwarded. To this end the electronics of the read-out board can be wired to the base board.

When solder contacting is used between the electrodes on the semiconductor and the read-out board, it should be noted here that widely-used solders, because of their usually relatively high melting point, can adversely affect semiconductor materials, for example in their crystal structure, which can have a negative effect on the resolution. In U.S. Pat. No. 6,933,505 B2 a solder contacting is specified for this for which essentially tin and bismuth is to be used as solder, so that a lower melting point of 138° C. is to be achieved.

It should also be noted that the read-out board is mostly manufactured as a wafer, e.g. made of silicon, on which the corresponding electronics is structured on one side, however the base board is to be contacted on the opposing side. An obvious wiring per se here has the result that the entire read-out board on the side of the read-out electronics cannot be covered by directly converting semiconductor material but that cutouts must be provided there for the wires. At these points the detector loses its resolution, which makes the construction of large, contiguous flat-panel detectors with much greater resolution significantly more difficult, since the size of individual semiconductor detection elements must be increased for this purpose.

DE 10 2008 050 838 A1 discloses a detector module with a radiation detector element, evaluation electronics and a common carrier substrate, which are soldered in layers in each case by way of a low-temperature solder. However this arrangement is also not capable of solving the aforementioned problem.

SUMMARY

At least one embodiment of the invention is directed to an imaging device for electromagnetic radiation, especially for x-ray and/or gamma radiation, which allows full coverage with a highest possible spatial resolution, wherein a high spectral resolution is also aimed for, and which has a high radiation sensitivity where possible only in the relevant spectral range.

At least one embodiment of the invention is directed to an imaging device for electromagnetic radiation, especially for x-ray and/or gamma radiation, which comprises a layered construction of a number of detection elements, a number of read-out boards and a base board, wherein the detection element or each detection element is electrically contacted via a plurality of first solder contacts, wherein the read-out board or each read-out board has a number of through-contacts and wherein the read-out board or each read-out board is contacted with the base board via a plurality of second solder contacts.

At least one embodiment of the invention further describes an x-ray detector, especially a photon-counting x-ray detector, which includes at least one imaging device of the previously described type. The advantages stated for the imaging device and its developments can in this case be transferred analogously to the x-ray detector.

BRIEF DESCRIPTION OF THE DRAWINGS

An example embodiment of the invention is explained in greater detail below with reference to a drawing. Each of the figures shows a schematic diagram:

FIG. 1 shows, in a cross-sectional diagram, a section of an x-ray detector in a conventional arrangement with a wired read-out board, FIG. 2 shows, in a cross-sectional diagram, a section of an x-ray detector with a through-contacted read-out board, and FIG. 3 shows an x-ray detector in a cross-sectional diagram and in an overhead view.

Parts and variables which correspond to one another are provided with the same reference characters in all figures.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium or non-transitory computer readable medium. A processor(s) will perform the necessary tasks.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the following description, illustrative embodiments may be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware at existing network elements. Such existing hardware may include one or more Central Processing Units (CPUs), digital signal processors (DSPs), application-specific-integrated-circuits, field programmable gate arrays (FPGAs) computers or the like.

Note also that the software implemented aspects of the example embodiments may be typically encoded on some form of program storage medium or implemented over some type of transmission medium. The program storage medium (e.g., non-transitory storage medium) may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

At least one embodiment of the invention is directed to an imaging device for electromagnetic radiation, especially for x-ray and/or gamma radiation, which comprises a layered construction of a number of detection elements, a number of read-out boards and a base board, wherein the detection element or each detection element is electrically contacted via a plurality of first solder contacts, wherein the read-out board or each read-out board has a number of through-contacts and wherein the read-out board or each read-out board is contacted with the base board via a plurality of second solder contacts.

A detection element here is to be understood as a device which creates electrical signals from an incident electromagnetic radiation. In particular the detection element or each detection element can convert the incident radiation free from scintillators directly into electrical signals. In particular in such cases the detection element can have an essentially flat geometry, and especially in such cases the signals can be output on the side facing away from the radiation incidence, wherein preferably, from the spatial distribution and the intensity of the signals a deduction about the corresponding characteristics of the incident radiation is possible.

A read-out board here is to be understood as a board to which read-out electronics for the signals created by a detection element is attached. For example the read-out electronics can involve an ASIC. The read-out board itself can be fabricated from a wafer, especially a silicon wafer for example.

Preferably the first solder contacts and the second solder contacts here are embodied free from further components such that an electrical connection between the detection element and the read-out board or between the read-out board and the base board only leads via the respective solder.

Preferably low-temperature solders are to be used for the first solder contacts and/or the second solder contacts, wherein the respective solders are preferably to be selected so that the highest melting point occurring in the manufacturing process of the imaging device for the components to be contacted, especially for the detection element or each detection element, does not represent any adverse effect in respect of functional capability. In particular the solders are to be selected so that, in the manufacturing process of the imaging device, first of all the solder contacts with the higher melting point can be made, so that a subsequent contact with a further solder can be carried out at a lower temperature and thus the firmness of the solder contacts already attached is not adversely effected.

Considerations underlying at least one embodiment of the invention here are as follows:

The key for a highest possible spatial resolution is first of all the detection element subjected to the incident radiation, this is thus to be embodied accordingly. The read-out board which is contacted with a detection element via solder contacts and can thus further process the signals created by the element, in particular makes possible here the use of a direct-converting or quanta-counting detection element, which allows an especially high spatial resolution. A high radiation sensitivity in the relevant spectral range is also made possible by this, while the radiation sensitivity in undesired spectral ranges can be greatly suppressed by a skillful choice of the detection element or each detection element compared to a detection based on scintillation, in which often so-called dark currents are caused by diffusion of the residual light of the environment.

The signals created in the detection element or in each detection element by incident radiation are to be forwarded by the read-out board to a higher-ranking application, which further processes the image signals. The base board, which in addition lends stability in the layering of the structure, is provided in the imaging device for this purpose.

The read-out electronics of the read-out board which receives the signals created by the detection element or by each detection element is facing towards the element in the layering. For the purpose of forwarding the signals via the base board this is thus preferably to be contacted with the read-out electronics on the read-out board.

This could be done via wiring in which individual signal channels of the read-out electronics are connected via a port attached to the read-out board to a corresponding port on the base board by a wire or a cable. For this individual signal channels could if necessary also be grouped together on the read-out board. Any wiring however requires a corresponding terminal on the side of the read-out board facing towards the detector element. At such a terminal the read-out board would then have to be kept free from the detection element, which would undermine a full coverage homogeneous resolution capability of the imaging device. Likewise wires or cables which lead past the sides of the read-out boards to the base board would increase the lateral spacing at which read-out boards each layered with a detection element and correspondingly contacted could be arranged next to one another on the base board. This is likewise undesired.

A surprising discovery for at least one embodiment of the invention is now to achieve the connections from the read-out electronics on one side of the read-out board to the base board on the opposite side initially via through-contacts through the read-out board or each read-out board, which are contacted in each case via solder contacts to the base board.

In particular in the arrangement of the first solder contacts and the second solder contacts as well as the through-contacts, a possible interaction in the manufacturing process, for example by a capillary action or similar, is to be taken into account.

Preferably a plurality of through-contacts each has a hole through the read-out board, the inner wall of which is clad with a conductive material. In this way the through-contacts can be manufactured especially easily. Copper or an alloy containing copper is preferably used here as the conductive material. Depending on technical requirements however different forms of embodiment for the through-contacts in a read-out board can be provided in parallel to one another.

Expediently the detection element or each detection element has a conversion layer in each case, to which on one side the plurality of contact pins is attached, wherein each contact pin is contacted via a first solder contact with the respective read-out board. In the conversion layer in such cases incident electromagnetic radiation can initially be converted to electron hole pairs, which can then be tapped off at the contact pins as electrical signals. The individual contact pins thus correspond to the respective pixels.

For a high spatial resolution of the imaging device it is therefore advantageous to arrange a plurality of contact pins that are as small as possible over as full an area of the conversion layer as possible, wherein it should be noted that within the conversion layer a cross-diffusion of the charge carriers (i.e. the electron hole pairs) which is as small as possible takes place. The result to be achieved by this is that a signal created at a contact pin can be assigned as uniquely as possible to an incident radiation quantum in the immediate vicinity on the opposite side on the conversion layer. The thickness of the conversion layer here is preferably to be selected so that incident radiation can create sufficient charge carriers and thus a sufficient signal strength, but that a cross-diffusion of the charge carriers which is as small as possible is to be expected.

It proves advantageous here for the or for each conversion layer essentially to be manufactured from at least one semiconductor material, wherein the or each semiconductor material is taken from a group which consists of the following compounds: cadmium telluride, zinc telluride, cadmium selenide, zinc selenide, manganese telluride, indium phosphide, mercury(II)-iodide and thallium(I,III)-bromide. These semiconductor materials mentioned, especially in the x-ray and in the Gamma spectral range, have a high effective cross-section and thus a high probability of interaction, which on the one hand allows a small thickness of the conversion layer with high-resolution, on the other hand also results in a high radiation sensitivity in the aforementioned spectral range. This is especially of advantage in medical applications, if for an imaging method a patient is to be subjected to the smallest possible radiation dose.

In an advantageous embodiment of the invention, as solder for the first solder contacts, at least one material is selected from a group which consists of Tin-bismuth, tin-bismuth-silver, tin-bismuth-lead, tin-indium, indium-silver and indium. In respect of a low melting point especially useful alloys are 58Sn42Bi, 57Sn42Bi1Ag and 97In3Ag, wherein the numerical specifications relate to percentages by weight. Pure indium is also advantageous as a solder in this regard. In further alloys a proportion in each case of between 30% and 60% of tin, bismuth or lead or a proportion of between 10% and 60% of tin and between 40% and 90% of indium proves useful. The specified materials have a comparatively low melting point as solder through which components to be contacted in the manufacturing processes, especially the detection element or each detection element, do not have to be exposed to higher temperatures, which could lead there to a change of the material structure and could have a disadvantageous effect on its resolution capabilities. This can be suppressed by using one of the low-temperature solders.

In a further embodiment of the invention, as solder for the second solder contacts, at least one material is used from the group which consists of: Tin-bismuth, tin-bismuth-silver, tin-bismuth-lead, tin-indium, indium-silver and indium. Especially advantageous mixture relationships for the alloys are those which are also mentioned for the first solder contacts. A use of one of the specified materials, which have a comparatively low melting point, as solder for the second solder contacts can be especially advantageous if, for process technology or cost reasons, a solder with a higher melting point is to be used for the first solder contacts in each case, and the first solder contacts are to be made first in the manufacturing process.

Preferably the detection element or each detection element is formed by a plate which has a polygonal shape, wherein the corresponding read-out plate contacted with the detection element essentially covers the same area. A layering on the base board which is formed from detection elements of a polygonal shape and read-out boards covering the same area as the elements makes it possible to dispose individual detection elements or read-out boards at their respective edges directly adjacent to one another, through which in the corresponding area a consistently high resolution capability of the imaging device is guaranteed. For the option of such an arrangement the through-contacts in the read-out boards are significant.

In an advantageous manner in this case at least one part area of the base board is covered essentially completely by a plurality of detection elements or the corresponding read-out boards. This should mean that, at least in this part area, the corresponding detection elements or the read-out boards lying below them are always disposed in each case without gaps at their edges adjacent to one another and thus a parquet arrangement of the plane in this part area is reached by the detection elements or the read-out boards. Through this in the corresponding part area of the layering on the base board a consistently high resolution capability of the imaging device is guaranteed. Preferably the part area is convex.

It also proves advantageous here for the detection elements, which essentially completely cover at least a part area of the base board, to each have a rectangular shape. In particular the corresponding read-out boards also have a rectangular shape. In particular in such cases a plurality of detection elements can cover the same area in each case. A rectangular form of the components to be layered on the base board—the detection elements and the read-out boards—allows a part area of the base board to be covered especially easily, so that the manufacturing process is simplified.

At least one embodiment of the invention further describes an x-ray detector, especially a photon-counting x-ray detector, which includes at least one imaging device of the previously described type. The advantages stated for the imaging device and its developments can in this case be transferred analogously to the x-ray detector.

FIG. 1 shows a cross-sectional diagram of the section of an imaging device 1 for electromagnetic radiation, which is embodied here as an x-ray detector 2 in a conventional arrangement. The x-ray detector 2 has a detection element 4, a read-out board 6 and a base board 8. The detection element 4 in this case is essentially formed by a conversion layer 10, which can be manufactured from a semiconductor material, for example CdTe or CdZnTe. The read-out board 6 is embodied as an ASIC. On the side facing towards the read-out board 6 the detection element 4 has individual contact pins 12, which are contacted in each case with the read-out electronics 14 disposed on the read-out board 6 via first solder contacts 16. The read-out electronics 14, which can be embodied for example as a CMOS applied to the substrate of the ASIC, is contacted with the base board 8 via a wire connection 18.

Incident x-ray radiation now creates electron hole pairs in the conversion layer 10 through band transitions in the semiconductor material. These are spatially largely localized in the area of the radiation instance. The charge carriers are tapped off in accordance with their spatial distribution at individual contact pins 12 as electrical signals. For this purpose a voltage can be applied if necessary to the detection element 4. The electrical signals are forwarded from the contact pins 12 via the first solder contacts 16 to the read-out electronics 14, if necessary further processed there, and a signal of the read-out electronics 14 is sent from the read-out board 6 via the wire connection 18 to the base board 8. Since the wire connection 18 needs space for connection to the read-out electronics 14, the read-out board 6 cannot be covered by the detection element 4 at this point. This adversely affects a full-coverage spatial resolution capability of the x-ray detector 2.

FIG. 2 shows a cross-sectional diagram of the section of an x-ray detector 2 which makes do without wiring of the read-out electronics 14 to the base board 8. The signals which are created in the conversion layer 10 by the radiation striking the detection element 4 and are forwarded via the contact pins 12 and the first solder contacts 16 to the read-out electronics 14, can be conveyed here after a possible further processing in the read-out electronics 14 by way of through-contacts 20 in the read-out board 6 on the underside 22 of the read-out board 6 facing towards the base board 8. The through-contacts 20 essentially consist of holes in the read-out board 6, which are clad with a conductive material, such as copper for example. The underside 22 of the read-out board 6 is contacted via second solder contacts 24 with the base board 8, so that the signal path leads from the read-out electronics 14 to the base board 8 via at least one through-contact 20 and at least one second solder contacting 24.

The through-contacts 20 thus replace wiring between the read-out electronics 14 and the base board 8. This means that it is not necessary to leave a cutout free for the connection of wiring on the read-out board 6, so that the board can be completely covered by detection element 4.

In the example embodiment in this case the read-out electronics 14 is disposed on the side of the read-out board 6 facing towards the detection element. A realization with read-out electronics 14 which is attached to the underside of the read-out board 6 is likewise possible as a result of the through-contacts 20.

The advantage of the arrangement described in FIG. 2 becomes clear in FIG. 3: Here an x-ray detector 2 is shown in a cross-sectional diagram and in an overhead view, in which a number of detection elements 4 with their associated read-out boards 6 are arranged into an array on the base board 8. Since the detection elements 4 completely cover the respective read-out board 6, and no space for connections of wiring is necessary on the read-out board 6, the x-ray detector 2 in the contiguous part area 26 has a full-coverage high resolution. Possible detection losses at the edges of two adjacent detector elements 4 are negligible by comparison with the cutouts.

A low-temperature solder, for example SnBi or SnBiAg, is to be used for the first solder contacts 16 here, in order not to adversely affect the crystal structure of the conversion layer 10 through high temperatures during soldering, which could have a disadvantageous effect on the conversion efficiency. In the selection of a solder for these second solder contacts 24 the order of the contacting of detection layer 4 and read-out boards 6 on the base board 8 is to be observed in the manufacturing process. For the production of the array it can be of advantage to first contact the detection elements 4 in each case with the read-out electronics 14 of the corresponding read-out board 6 into stacks and then to contact the stacks in each case on the base board 8. In this case it would have to be taken into account that the solder for the second solder contacts 24 preferably has a lower melting point than the solder for the first solder contacts 16.

Although the invention has been illustrated and described in greater detail by the preferred example embodiment, the invention is not restricted by this example embodiment. Other variations can be derived herefrom by the person skilled in the art, without departing from the scope of protection of the invention.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An imaging device for electromagnetic radiation, the imaging device comprising:
a layered structure including
a plurality of individual detection elements,
a plurality of read-out boards, and
a base board; wherein
each respective detection element among the plurality of individual detection elements corresponds to a respective read-out board among the plurality of read-out boards,
each respective read-out board includes read-out electronics on an external surface thereof, the external surface being a surface of the respective read-out board most proximate to a surface of the respective detection element corresponding to the respective read-out board, the read-out electronics configured to read out signals generated by the respective detection element corresponding to the respective read-out board,
each respective detection element includes at least one contact pin physically contacting a corresponding one of a plurality of first solder contacts, the corresponding one of the plurality of first solder contacts also physically contacting the read-out electronics of the respective read-out board corresponding to the respective detection element,
each respective read-out board further includes a plurality of through-contacts carrying data signals, the plurality of through-contacts passing entirely through the respective read-out board, the plurality of through-contacts being centrally located relative to an array of the plurality of first solder contacts on the respective read-out board, and the plurality of through-contacts being spaced evenly across the entire respective read-out board, and
each respective read-out board is electrically connected with the base board via a plurality of second solder contacts.

2. The imaging device of claim 1, wherein
an inner wall of each of the plurality of through-contacts is clad with a conductive material.

3. The imaging device of claim 2, wherein
each respective detection element includes a conversion layer;
a plurality of contact pins are attached to a side of the conversion layer; and
each respective detection element is connected with the corresponding respective read-out board via the array of the plurality of first solder contacts and the plurality of contact pins.

4. The imaging device of claim 3, wherein
each respective conversion layer includes at least one semiconductor material; and
the at least one semiconductor material includes at least one of cadmium telluride, zinc telluride, cadmium selenide, zinc selenide, manganese telluride, indium phosphide, mercury(II)-iodide and thallium(I,III)-bromide.

5. The imaging device of claim 2, wherein the plurality of first solder contacts include at least one of tin-bismuth, tin-bismuth-silver, tin-bismuth-lead, tin-indium, indium-silver and indium.

6. The imaging device of claim 2, wherein the plurality of second solder contacts include at least one of tin-bismuth, tin-bismuth-silver, tin-bismuth-lead, tin-indium, indium-silver and indium.

7. The imaging device of claim 2, wherein
each respective detection element includes a plate having a polygonal shape; and
each respective detection element covers substantially the same area as the corresponding respective read-out board.

8. The imaging device of claim 7, wherein at least a portion of the base board is substantially covered by the plurality of individual detection elements or corresponding ones of the plurality of read-out boards.

9. The imaging device of claim 8, wherein each of the plurality of individual detection elements has a rectangular shape.

10. The imaging device of claim 1, wherein
each respective detection element includes a conversion layer;
a plurality of contact pins are attached to a side of the conversion layer; and
each respective detection element is connected with the corresponding respective read-out board via the array of the plurality of first solder contacts and the plurality of contact pins.

11. The imaging device of claim 10, wherein
each respective conversion layer includes at least one semiconductor material; and
the at least one semiconductor material includes at least one of cadmium telluride, zinc telluride, cadmium selenide, zinc selenide, manganese telluride, indium phosphide, mercury(II)-iodide and thallium(I,III)-bromide.

12. The imaging device of claim 1, wherein the plurality of first solder contacts include at least one of tin-bismuth, tin-bismuth-silver, tin-bismuth-lead, tin-indium, indium-silver and indium.

13. The imaging device of claim 12, wherein the plurality of second solder contacts include at least one of tin-bismuth, tin-bismuth-silver, tin-bismuth-lead, tin-indium, indium-silver and indium.

14. The imaging device claim 1, wherein the plurality of second solder contacts include at least one of tin-bismuth, tin-bismuth-silver, tin-bismuth-lead, tin-indium, indium-silver and indium.

15. The imaging device of claim 1, wherein
each respective detection element includes a plate having a polygonal shape; and
each respective detection element covers substantially the same area as the corresponding respective read-out board.

16. The imaging device of claim 15, wherein at least a portion of an area of the base board is substantially covered by the plurality of individual detection elements or corresponding ones of the plurality of read-out boards.

17. The imaging device of claim 16, wherein each of the plurality of individual detection elements has a rectangular shape.

18. An x-ray detector, including at least one imaging device of claim 1.

19. The x-ray detector of claim 18, wherein the x-ray detector is a photon-counting x-ray detector.

20. The imaging device of claim 1, wherein the electromagnetic radiation is at least one of x-ray and gamma radiation.

21. The imaging device of claim 1, wherein the plurality of first solder contacts have a higher melting point than the plurality of second solder contacts.

* * * * *